United States Patent [19]

Schilling

[11] 4,323,678
[45] Apr. 6, 1982

[54] PROCESS FOR THE MANUFACTURE OF DIAZINON

[75] Inventor: Bernd Schilling, Munich, Fed. Rep. of Germany

[73] Assignee: Consortium fur elektrochemische Ind. GmbH, Munich, Fed. Rep. of Germany

[21] Appl. No.: 120,411

[22] Filed: Feb. 11, 1980

[30] Foreign Application Priority Data

Feb. 28, 1979 [DE] Fed. Rep. of Germany ........ 2907773

[51] Int. Cl.³ .............................................. C07F 9/65
[52] U.S. Cl. .................................................... 544/243
[58] Field of Search ................................ 544/243, 319

[56] References Cited

U.S. PATENT DOCUMENTS

| | | | |
|---|---|---|---|
| 2,754,243 | 7/1956 | Gysin et al. | 544/243 X |
| 2,928,864 | 3/1960 | Tabor | 260/973 |
| 3,798,220 | 3/1974 | Klemm et al. | 544/243 X |
| 3,862,273 | 1/1975 | Kroposki et al. | 260/973 |
| 4,012,506 | 3/1977 | Balke et al. | 544/243 X |
| 4,052,397 | 10/1977 | Blackwell et al. | 544/319 |

FOREIGN PATENT DOCUMENTS

| | | | |
|---|---|---|---|
| 2055523 | 5/1971 | Fed. Rep. of Germany | 544/319 |
| 2065698 | 12/1974 | Fed. Rep. of Germany | 544/319 |
| 2011415 | 7/1979 | United Kingdom | 544/243 |

Primary Examiner—Donald G. Daus
Assistant Examiner—Diana G. Rivers
Attorney, Agent, or Firm—Allison C. Collard; Thomas M. Galgano

[57] ABSTRACT

The invention provides an improved process for the manufacture of the insecticide diazinon. The process uses β-isobutyrylaminocrotonic acid amide as starting material and, by reaction with sodium hydroxide solution or alcoholate and phosphorylation with diethylthiophosphoryl chloride, diazinon (0,0-diethyl-0-(2-isopropyl-4-methyl-6-pyrimidinyl)thiono -phosphate) is obtained directly in a high yield without isolating any intermediates.

4 Claims, No Drawings

PROCESS FOR THE MANUFACTURE OF DIAZINON

The present invention relates to an improved process for the manufacture of diazinon which, owing to its good insecticidal and acaricidal properties and its low toxicity with respect to warm-blooded animals, is widely used for the destruction of insect pests.

Diazinon was produced for the first time as early as 1952 by Glysin and Margot by reacting 2-isopropyl-4-methyl-6-hydroxypyrimidine with diethylthiophosphoryl chloride in an inert solvent in the presence of potassium carbonate:

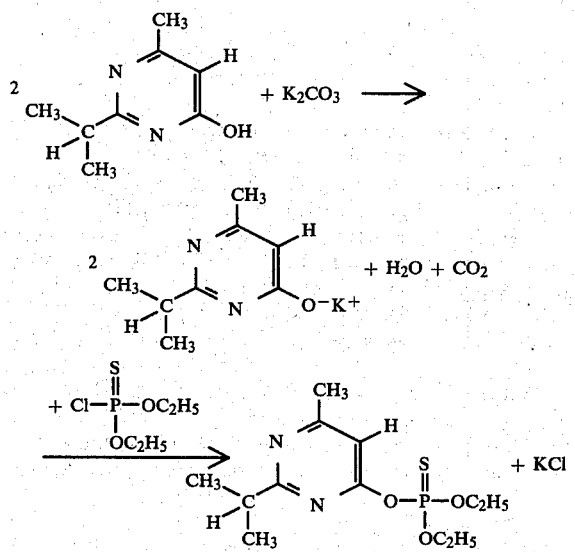

In this reaction, potassium pyrimidinolate is initially produced by heating 2-isopropyl-4-methyl-6-hydroxypyrimidine with potassium carbonate, for example, in benzene, with simultaneous removal of the water formed. The potassium salt, which is produced in this manner in the form of a finely divided suspension, is then reacted with diethylthiophosphoryl chloride by heating for several hours. When the reaction is complete, the potassium chloride formed is extracted by washing with water and the solvent is removed under reduced pressure (G.B. patent specification No. 713,278). The standard process for industrial manufacture is carried out essentially by means of a 4-stage synthesis according to the following reaction scheme:

1. Imido ester stage:

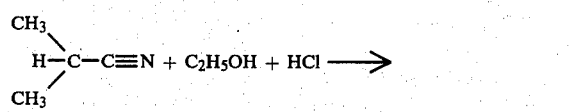

2. Amidine stage:

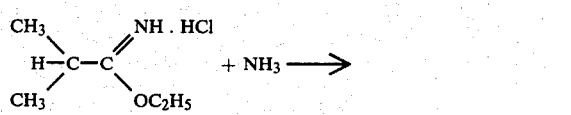

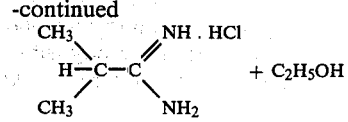

3. Cyclization:

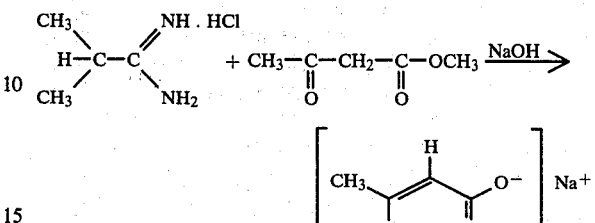

4. Neutralization stage:

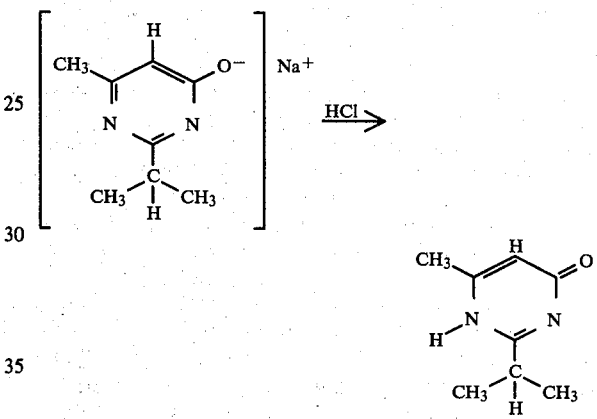

Although, in the meantime, a number of simpler processes have been described in the literature (cf. in this connection U.S. Pat. No. 4,052,397), these have clearly not, as yet, been carried out on an industrial scale.

Following the actual diazinon process previously described, there have been a number of supplementary patent specifications concerned especially with suitable catalyst systems for shortening the long reaction times of the original process. Suitable systems are, according to U.S. Pat. No. 3,107,245, e.g., mercury salts, according to U.S. Pat. No. 3,107,246, e.g., copper chloride, according to U.S. Pat. No. 3,367,935, copper nitrate, and according to Japanese Patent specification No. 7,524,958, basic copper oxide.

The problem underlying the present invention is to provide a manufacturing process that is simpler than the known processes and by means of which the synthesis of diazinon can be carried out, using readily available starting materials, in a single stage without the complicated isolation of intermediates.

This problem is solved by a process embodying the present invention that is characterized in that β-isobutyrylaminocrotonic acid amide is cyclized with 1 to 1.2 times the molar amount of a substance of the general formula NaOR, in which R represents hydrogen or an alkyl group having 1 to 8 carbon atoms, in a mixture of 0 to 100% by weight of water and an alcohol having 1 to 8 carbon atoms, above 90° C. but below the boiling point of the alcohol/water mixture used. The resulting sodium pyrimidinolate is precipitated by a non-polar solvent which is inert towards the alcoholate and which has a boiling point above that of the alcohol used, and is reacted directly with diethylthiophosphoryl chloride at a temperature of 100° to 130° C. to form diazinon.

The β-isobutyrylaminocrotonic acid amide used in the reaction is described in detail in the relevant technical literature and may be prepared, for example, by acylating β-aminocrotonic acid amide, which is readily available from diketene and ammonia (cf. DT-OS 2 037 888), with dimethyl ketone (cf. DT-OS 2 852 887) or isobutyric acid anhydride (cf. DT-OS 2 065 698).

According to the invention, it is possible to use as the substance of the general formula NaOR, sodium methylate, ethylate, propylate, butylate, pentylate, hexylate, heptylate, octylate or, preferably, sodium hydroxide solution. Cyclization is carried out in approximately 3 to 8 times the amount by weight, calculated on the starting material, of a mixture of 0 to 100% by weight of water and an alcohol having 1 to 8 carbon atoms. The upper limit for the quantity of water and alcohol is given because, although larger quantities by weight do not stop the reaction, they produce no recognizable advantages and so only increase costs unnecessarily. Generally, the mixtures of water and alcohol used should have boiling points above 90° C. since cyclization is effected at or above this temperature; that is to say the cyclization temperature and the boiling point of the mixture of water and alcohol must be coordinated.

According to a preferred embodiment, the reaction of β-isobutyrylaminocrotonic acid amide with sodium hydroxide solution is carried out in pure isobutanol since this can easily be removed by distillation. It is also possible to obtain yields of approximately 100%, however, using aqueous sodium hydroxide solution or, for example, sodium hydroxide solution or isobutanolate in isobutanol.

The cyclization is usually complete after approximately 1 to 3 hours; higher temperatures resulting in correspondingly shorter times.

To convert the sodium salt into a suspension suitable for phosphorylation, a portion of the mixture of water and alcohol, advantageously approximately 60 to 80% by weight, is initially distilled off, and a non-polar solvent which is inert towards the alcoholate and which has a boiling point above that of the alcohol used, such as, e.g., cyclohexane, ligroin, toluene or, preferably, xylene, is added.

The remaining alcohol and water are at least substantially fractionally distilled off at normal pressure. For example, isobutanol and water coordinatively bonded to the salt are removed at the temperatures necessary for this, i.e., at 120° to 130° C.

Then, without isolation, the precipitated sodium pyrimidinolate is reacted directly by the rapid addition of diethylthiophosphoryl chloride at a temperature of 100° to 130° C., preferably 115° to 120° C. to form diazinon. Depending on the temperature selected, the reaction is complete after a comparatively short time—for example, at 120° C. after approximately 1 hour. Working up is then carried out in the usual manner by extraction by washing with water and distilling off the solvent in vacuo after previously separating the water.

In the following Example, the process of the present invention will be more fully described, and is given by way of illustration and not of limitation.

EXAMPLE 170 g (1 mole) of β-isobutyrylaminocrotonic acid amide and 40 g (1 mole) of sodium hydroxide were heated in 1000 ml of isobutanol to 100° C. Subsequently, approximately 600 ml of isobutanol/reaction water were distilled off at normal pressure. After adding 1200 ml of xylene, the remaining isobutanol was removed by fractionation. 188.5 g (1 mole) of diethylthiophosphoryl chloride were then quickly added dropwise (3 minutes) at 120° C., while stirring, to the resulting sodium salt which was in the form of a voluminous, finely crystalline suspension. By cooling as necessary, the temperature was maintained for approximately 30 minutes and then lowered to 110° C. After a further 30 minutes the mixture was finally cooled to room temperature (25° C.).

The reaction mixture was then washed first with 400 ml of 0.1 N hydrochloric acid and then with 400 ml of 0.1 N sodium hydroxide solution. After separating off the washing liquids, the xylene was distilled off in vacuo. For the complete removal of the volatile constituents, the diazinon was finally distilled in a high vacuum (approximately 1 mbar) at 60° C. The yield of 0,0-diethyl-0-(2-isopropyl-4-methyl-6-pyrimidinyl)thionophosphate was 280 g $\hat{=}$ 92.1% of the theoretical yield.

While only one example of the present invention has been shown and described, it will be obvious that many modifications and changes may be made thereunto, without departing from the spirit and scope of the invention.

What is claimed is:

1. In a process for the manufacture of diazinon, the improvement comprising the steps of:
   cyclizing β-isobutyrylaminocrotonic acid amide with 1 to 1.2 times the molar amount of a substance of the general formula NaOR, in which R represents hydrogen or an alkyl group having 1 to 8 carbon atoms, in a mixture of 0 to 100% by weight of water and an alcohol having 1 to 8 carbon atoms, above 90° C. but below the boiling point of the alcohol/water mixture used;
   precipitating the resulting sodium pyrimidinolate by a non-polar solvent which is inert toward the alcoholate and which has a boiling point above that of the alcohol used; and
   after removing the alcohol/water mixture by fractionation, reacting the precipitated sodium pyrimidinolate directly with diethylthiophosphoryl chloride at a temperature of 100° to 130° C. to form diazinon.

2. The process according to claim 1, wherein sodium hydroxide solution is used as the substance of the general formula NaOR.

3. The process according to claim 2, wherein the reaction of β-isobutyrylaminocrotonic acid amide with sodium hydroxide solution is carried out in isobutanol.

4. The process according to claim 1, 2, or 3, wherein the sodium pyrimidinolate is precipitated by xylene.

* * * * *